(12) United States Patent
Hong et al.

(10) Patent No.: US 11,559,797 B2
(45) Date of Patent: Jan. 24, 2023

(54) ACYCLIC CARBENE LIGAND FOR RUTHENIUM COMPLEX FORMATION, RUTHENIUM COMPLEX CATALYST, AND USE THEREOF

(71) Applicant: GWANGJU INSTITUTE OF SCIENCE AND TECHNOLOGY, Gwangju (KR)

(72) Inventors: Sukwon Hong, Gwangju (KR); Seunghwan Byun, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 175 days.

(21) Appl. No.: 17/091,669

(22) Filed: Nov. 6, 2020

(65) Prior Publication Data
US 2021/0138443 A1 May 13, 2021

(30) Foreign Application Priority Data
Nov. 8, 2019 (KR) .................. 10-2019-0142835

(51) Int. Cl.
| | | |
|---|---|---|
| B01J 31/22 | (2006.01) | |
| B01J 37/04 | (2006.01) | |
| C07D 207/20 | (2006.01) | |
| C07D 209/08 | (2006.01) | |
| C07D 211/70 | (2006.01) | |
| C07F 15/00 | (2006.01) | |
| C07C 6/04 | (2006.01) | |
| C07C 251/30 | (2006.01) | |

(52) U.S. Cl.
CPC ....... *B01J 31/2278* (2013.01); *B01J 31/2226* (2013.01); *B01J 37/04* (2013.01); *C07C 6/04* (2013.01); *C07C 251/30* (2013.01); *C07D 207/20* (2013.01); *C07D 209/08* (2013.01); *C07D 211/70* (2013.01); *C07F 15/0046* (2013.01); *B01J 2231/48* (2013.01); *B01J 2231/543* (2013.01); *B01J 2531/004* (2013.01); *B01J 2531/821* (2013.01); *C07C 2531/12* (2013.01)

(58) Field of Classification Search
None
See application file for complete search history.

(56) References Cited

FOREIGN PATENT DOCUMENTS

KR   10-2019-0120240 A   10/2019

OTHER PUBLICATIONS

Koganty et al. "Reactions of acid halides and chloroformates involving an intermediate with dimethylformamide" Tetrahedron Letters, 1973, vol. 14, No. 45, pp. 4511-4514.*

* cited by examiner

*Primary Examiner* — Joseph R Kosack
(74) *Attorney, Agent, or Firm* — Hauptman Ham, LLP

(57) ABSTRACT

Provided are a novel acyclic carbene ligand for ruthenium complex formation; a ruthenium complex catalyst using the ligand; a method of using the complex as a catalyst in an ethylene-metathesis ethenolysis reaction; a method of preparing the ruthenium complex catalyst; and a method of preparing a linear alpha-olefin, the method including the step of reacting a linear or cyclic alkene compound in the presence of the ruthenium complex catalyst.

The acyclic carbene ligand of the present invention and the ruthenium complex catalyst using the same have high selectivity and turnover number for terminal olefin formation in an ethylene-metathesis ethenolysis reaction, and thus linear α-olefins may be prepared with a high yield.

11 Claims, 2 Drawing Sheets

ACYCLIC CARBENE LIGAND FOR RUTHENIUM COMPLEX FORMATION, RUTHENIUM COMPLEX CATALYST, AND USE THEREOF

CROSS-REFERENCE TO RELATED APPLICATION

This application claims priority under 35 U.S.C. § 119 to Korean Patent Application No. 10-2019-0142835, filed on Nov. 8, 2019 in the Korean Intellectual Property Office (KIPO), the contents of which are herein incorporated by reference in their entirety.

BACKGROUND OF THE INVENTION

1. Field of the Invention

The present invention relates to a novel, acyclic carbene ligand for ruthenium complex formation; a ruthenium complex catalyst using the ligand; a method of using the complex as a catalyst in an ethylene-metathesis ethenolysis reaction; a method of preparing the ruthenium complex catalyst; and a method of preparing a linear alpha-olefin, the method including the step of reacting a linear or cyclic alkene compound in the presence of the ruthenium complex catalyst.

2. Description of the Related Art

Known since 1977, the Shell Higher Olefin Process (SHOP) is a method of synthesizing linear α-olefins obtained from petrochemical raw materials. The Shell Higher Olefin Process has a problem in that linear α-olefins have a wide distribution, with 41% of linear α-olefins having 4 to 8 carbon atoms, 40.5% of linear α-olefins having 10 to 18 carbon atoms, and 18.5% of linear α-olefins having 20 or more carbon atoms. For example, the Snell Higher Olefin Process has a problem of a low synthesis yield of 1-decene. In addition, this method requires a high temperature of 60° C. to 300° C. and a high pressure of 30 bar to 200 bar.

In one aspect to solve these problems, research, and development are actively being conducted on ruthenium complex catalysts for olefin metathesis. The Grubbs catalyst, awarded the Nobel Prize in Chemistry in 2005, is known as a ruthenium complex catalyst.

Meanwhile, for the preparation of linear α-olefins, natural seed oil may be used instead of petroleum raw materials. For example, a method of synthesizing linear α-olefins from renewable seed oil as a raw material is as follows. Cross-metathesis of methyl oleate with ethylene may be performed. C=C double bonds are decomposed by ethenolysis of methyl oleate. Accordingly, it is possible to synthesize a desired linear α-olefin. Unlike the Shell Higher Olefin Process described above, the synthesis yield of a single 1-decene is high. In addition, unlike the Shell Higher Olefin Process described above, cross-metathesis using a Ru catalyst is advantageous in that it may be performed at a low temperature of 40° C. to 100° C. and at a low pressure of about 10 bar.

Further, a ruthenium complex catalyst having a N heterocyclic carbene (NHC) ligand, is known. The ruthenium complex having an asymmetrically substituted N-heterocyclic carbene ligand exhibits high selectivity for cross-metathesis products over self-metathesis by-produces, and thus it has been identified as a promising catalyst for ethenolysis. Stabilization of a methylidene intermediate has been suggested as a key factor in enhancing catalytic activity.

An additional electron-donating ligand is known to help stabilize the methylidene intermediate, but there is a problem in that a phosphine ligand undergoes decomposition by way of phosphine.

Meanwhile, imidazo [1,5-a]pyridine-3-ylidene (ImPy) which was first reported in 2005 is a candidate for the structurally asymmetric NRC ligand and has various electronic properties.

However, the above catalysts still have low selectivity for the formation of terminal olefins, and thus there is a need for the development of a new catalyst. In addition, a catalyst using a cyclic carbene ligand is known (Korean Patent Application No. 10-2019-7026049), but there has been no report regarding a ruthenium catalyst using an acyclic carbene ligand as in the present invention.

Accordingly, the present inventors have developed a novel acyclic aminooxycarbene ligand having high catalytic activity, high selectivity for the formation of terminal olefins in ethenolysis of methyl oleate, and high stability, thereby completing a ruthenium complex ligand and a ruthenium complex.

SUMMARY OF THE INVENTION

An object of the present invention is to provide an acyclic carbene ligand for the formation of a ruthenium complex, the acyclic carbene ligand having a structure of the following Chemical Formula 1:

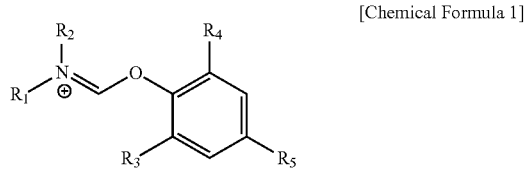

[Chemical Formula 1]

wherein, in Chemical Formula 1, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, and $R_5$ is a hydrogen atom or $C_1$-$C_6$ alkyl group.

Another object of the present invention is to provide a ruthenium complex catalyst having a structure of the following Chemical Formula 3:

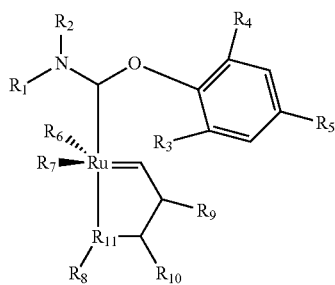

[Chemical Formula 3]

wherein, in Chemical Formula 3, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, $R_6$ and $R_7$ are each independently a halogen, $R_8$ is a substituted or unsubstituted $C_1$-$C_{10}$ alkyl group, $C_5$-$C_{10}$ carbocycle, or 5- to 10-membered heterocycle, $R_9$ and $R_{10}$ are each independently a $C_1$-$C_{10}$ alkyl group, or are connected to each other to form a $C_5$-$C_{10}$ carbocycle or a 5- to 10-membered heterocycle, and $R_{11}$ is N or O.

Still another object of the present invention is to provide a method of using the ruthenium complex as a catalyst in ethylene-metathesis ethenolysis of a linear or cyclic alkene compound.

Still another object of the present invention is to provide a method of preparing a ruthenium complex catalyst, the method including the steps of treating formamide with oxalyl chloride ($(COCl)_2$) to obtain an intermediate; reacting the intermediate with alkoxysilane (RORMS) to obtain an acyclic carbene ligand having a structure of Chemical Formula 1; and binding the ligand with ruthenium (Ru) to form a ruthenium complex catalyst having a structure of Chemical Formula 4.

Still another object of the present invention is to provide a method of preparing a linear alpha-olefin (linear α-olefin), the method including the step of reacting a linear or cyclic alkene compound in the presence of the ruthenium complex catalyst.

DETAILED DESCRIPTION OF THE PREFERRED EMBODIMENTS

Figure 1:
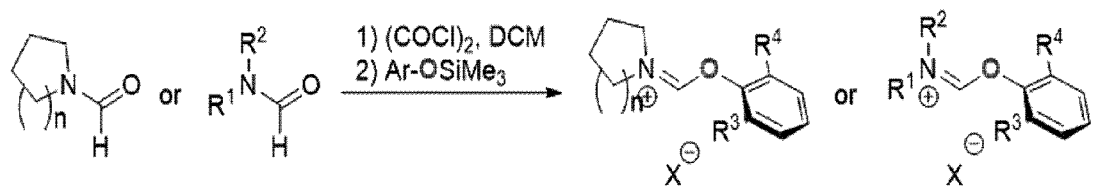
FIG. 1 illustrates an acyclic carbene ligand and a reaction scheme for producing a ruthenium complex catalyst using the same.
Figure 1:
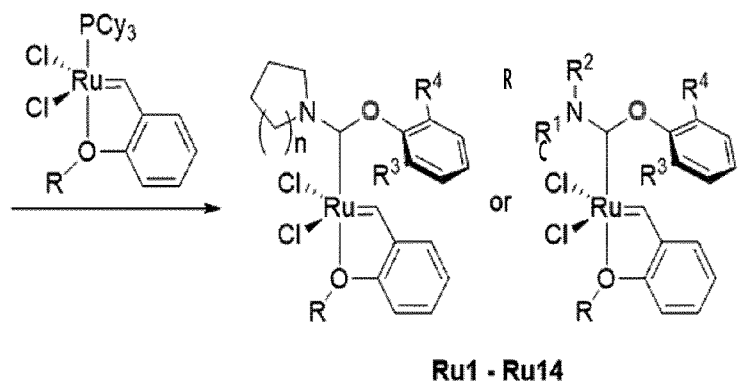

Hereinafter, the present invention will be described in detail. Meanwhile, each description and embodiment disclosed in this disclosure may also be applied to other descriptions and embodiments. That is, all combinations of various element s disclosed in this disclosure fall within the scope of the present invention. Further, the scope of the present invention is not limited by the specific description described below.

To achieve the above object, an aspect of the present invention provides an acyclic carbene ligand for the formation of a ruthenium (Rn) complex, the acyclic carbene ligand having a structure of the following Chemical Formula 1:

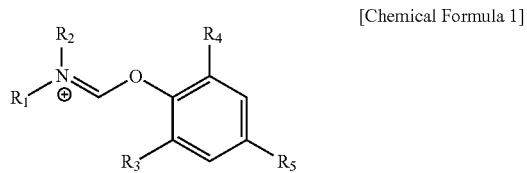

[Chemical Formula 1]

wherein, in Chemical Formula 1, $R_1$ and $R_2$ are each independently a hydrogen atom, a substituted or unsubstituted alkyl group, a substituted or unsubstituted cycloalkyl group, a substituted or unsubstituted aryl group; or $R_1$ and $R_2$ are connected to each other to form an unsubstituted or substituted heterocycle with a nitrogen atom to which they are connected, $R_3$ and $R_4$ are each independently a hydrogen atom, a substituted or unsubstituted alkyl group, alkenyl group, alkynyl group, a substituted or unsubstituted cycloalkyl group, or a substituted or unsubstituted aryl group, and $R_5$ is a hydrogen atom or alkyl group.

More specifically, the acyclic carbene ligand, for the formation of the ruthenium complex has the structure of Chemical Formula 1, wherein $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, and $R_5$ is a hydrogen atom or $C_1$-$C_6$ alkyl group.

The acyclic carbene ligand for the formation of the ruthenium complex may have a structure of the following Chemical Formula 2:

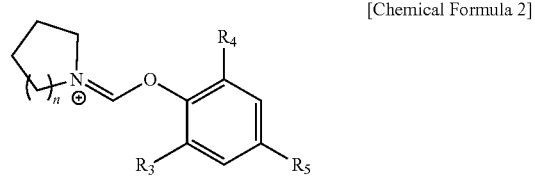

[Chemical Formula 2]

wherein, in Chemical Formula 2, n is an integer of 0 or more, $R_3$ and $R_4$ are each independently a hydrogen atom, a substituted or unsubstituted alkyl group, alkenyl group, alkynyl group, a substituted or unsubstituted cycloalkyl group, a substituted or unsubstituted aryl group, and $R_5$ is a hydrogen atom or alkyl group.

More specifically, the acyclic carbene ligand for the formation of the ruthenium complex has the structure of Chemical Formula 2, wherein n is an integer of 0 to 4, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, and $R_5$ is a hydrogen atom or $C_1$-$C_6$ alkyl group.

Further, specifically, the acyclic carbene ligand for the formation of the ruthenium complex has the structure of Chemical Formula 2, wherein n is an integer of 1 or 2, and $R_3$ and $R_4$ may be propyl, butyl, or diphenylmethyl, but are not limited thereto.

As used herein, the term "acyclic carbene ligand (acyclic aminooxycarbene)" or "carbene ligand" refers to a compound having a structure in which N—C—O is connected in an acyclic form, and is a novel carbene ligand which has not been disclosed. The acyclic carbene ligand forms a complex with ruthenium to be used as a catalyst in ethylene-metathesis ethenolysis, and this use was also first identified in the present invention.

Specifically, the acyclic carbene ligand has high selectivity and turnover, as compared with a cyclic carbene ligand or a N—C—N acyclic carbene (acyclic diaminocarbene) ligand, and can thereby prepare linear alpha-olefins with high yield.

The term "selectivity" may mean that cross-metathesis products are produced in a high ratio, as compared with self-metathesis by-products, in the ethylene-metathesis ethenolysis, and in particular, terminal olefins are produced in a high ratio, but the term is not limited thereto.

In one exemplary embodiment of the present, invention, it was confirmed that when ethenolysis is performed using the ruthenium complex catalyst having the acyclic carbene ligand of the present invention, the yield of linear alpha-olefins may be increased due to high selectivity.

To achieve the above object, another aspect of the present invention provides a ruthenium complex catalyst having a structure of the following Chemical Formula 3, the ruthenium complex catalyst using the acyclic carbene ligand:

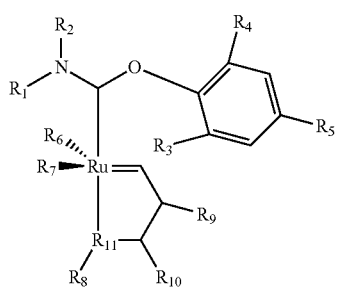

[Chemical Formula 3]

wherein, in Chemical Formula 3, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, $R_6$ and $R_7$ are each independently a halogen, $R_8$ is a substituted or unsubstituted $C_1$-$C_{10}$ alkyl group, $C_6$-$C_{10}$ carbocycle, or 5- to 10-membered heterocycle, $R_9$ and $R_{10}$ are each independently a $C_1$-$C_{10}$ alkyl group, or are connected with each other to form a $C_5$-$C_{10}$ carbocycle or a 5- to 10-membered heterocycle, and $R_{11}$ is N or O.

Specifically, the alkyl and alkoxy are each independently substituted or unsubstituted with at least one of a halogen, hydroxyl, and amino group;

the carbocycle and heterocycle are each independently a saturated or unsaturated ring of a single or double ring, which is substituted or unsubstituted with at least one selected from the group consisting of a halogen, a nitro group, a $C_1$-$C_5$ alkyl group, a halo ($C_1$-$C_5$ alkyl) group, a $C_1$-$C_5$ alkoxy group, and a phenyl group; and the heterocycle includes at least one heteroatom selected from N, S, and O.

To achieve the above object, still another aspect of the present invention provides a ruthenium complex catalyst having a structure of the following Chemical Formula 4, the ruthenium complex catalyst using the acyclic carbene ligand:

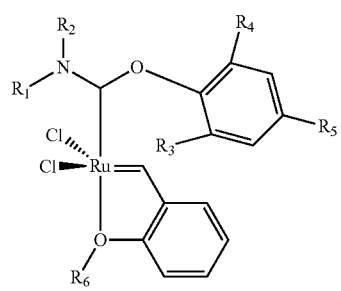

[Chemical Formula 4]

wherein, in Chemical Formula 4, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, and $R_8$ iS a substituted or unsubstituted $C_1$-$C_{10}$ alkyl group, $C_5$-$C_{10}$ carbocycle, or 5- to 10-membered heterocycle.

The ruthenium complex catalyst may have a structure of the following Chemical Formula 5:

[Chemical Formula 5]

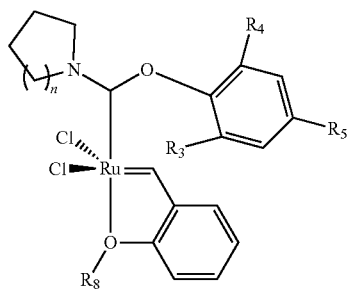

wherein, in Chemical Formula 5,
n is an integer of 0 to 4,
$R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group,
$R_5$ is a hydrogen atom or $C_1$-$C_6$ alkyl group, and
$R_8$ is a substituted or unsubstituted $C_1$-$C_{10}$ alkyl group, $C_5$-$C_{10}$ carbocycle, or 5- to 10-membered heterocycle.

Specifically, the ruthenium complex catalyst has the structure of Chemical Formula 5,
wherein n is an integer of 1 or 2, and
$R_3$ and $R_4$ may be propyl, butyl, or diphenylmethyl, but is not limited thereto.

As used herein, the term "ruthenium complex catalyst" or "ruthenium catalyst" may mean that the acyclic carbene ligand and ruthenium (Ru) metal produce a complex (a complex compound) to be used as a catalyst in the ethylene-metathesis ethenolysis reaction.

Figure 3:
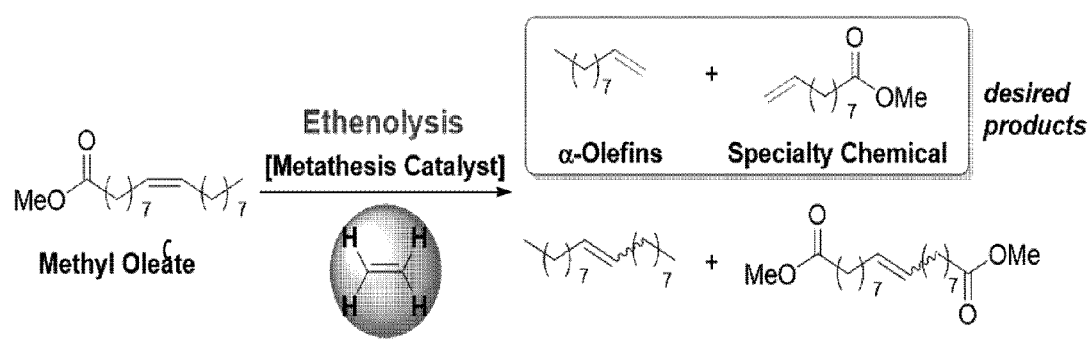
FIG. 3 shows ethenolysis of methyl, oleate as a specific exemplary embodiment of ethenolysis.

In one exemplary embodiment of the present invention, it was confirmed that when the unsubstituted or substituted 4- to 8-membered heterocycle is formed with a nitrogen atom in the structure of Chemical Formula 4 of the ruthenium complex catalyst, the selectivity is increased, and in particular, when a 5- or -6 membered heterocycle including the nitrogen atom is formed, corresponding to the case where n is an integer of 1 or In this regard, the "ethenolysis reaction", which is a metathesis reaction using ethylene, may mean a reaction that breaks internal olefins to convert them into terminal olefins. Specifically, the ethenolysis reaction may refer to a method of preparing an alpha-linear olefin by using a linear or cyclic alkene compound as a reactant, but is not limited thereto. A specific example of the ethenolysis reaction is an ethenolysis reaction of methyl oleate, as illustrated in FIG. 3.

The ethenolysis reaction has been suggested as a new method of preparing linear alpha-olefins from oils existing in nature, not through a petrochemical process.

In addition, according to recent studies, a ruthenium complex having a N-heterocyclic carbene (NHC) ligand has been studied as one of the catalysts for ethenolysis, but it still has higher selectivity for desired linear α-olefins than self-metathesis by-products, and there is still a need for the development of catalysts to improve reaction efficiency.

In one exemplary embodiment of the present invention, it high selectivity and reaction efficiency are achieved in the production of linear alpha-olefins via the ethenolysis reaction.

As used herein, the term "linear olefin" or "alpha-olefin" or "linear alpha-olefin (linear α-olefin)", which is a product of the ethenolysis reaction, may specifically refer to an olefin having a Chemical Formula of $C_xH_{2x}$.

Specifically, the linear alpha-olefin may include 1-butene, 1-hexene, 1-octene, 1-decene, 1-dodecene, 1-tetradecene, 1-hexadecene, 1-octadecene, and $C_{20}$-$C_{24}$, $C_{24}$-$C_{30}$, and $C_{20}$-$C_{30}$ olefins, but is not limited thereto.

The linear alpha-olefin may be used as a very useful-intermediate in the production of detergents, synthetic lubricants, copolymers, plasticizers, and many other important products.

To achieve the above object, still another aspect of the present invention provides a method of using the ruthenium complex as a catalyst in the ethylene-metathesis ethenolysis reaction of a linear or cyclic alkene compound.

In this regard, the term "ruthenium complex" and "ethenolysis" are the same as described above.

A specific example of the ethylene-metathesis ethenolysis reaction is an ethenolysis reaction of methyl oleate, as illustrated in FIG. 3, and any example may be included, as long as it is the ethenolysis reaction, but the reaction is not limited thereto.

To achieve the above object, still another aspect of the present invention provides a method of preparing the ruthenium complex catalyst, the method including the steps of:
treating formamide with oxalyl chloride (($COCl)_2$) to obtain an intermediate; reacting the intermediate with alkoxysilane (ROTMS) to obtain an acyclic carbene ligand having the structure of Chemical Formula 1; and binding the ligand with ruthenium (Ru) to form a ruthenium complex catalyst having the structure of Chemical Formula 4:

[Chemical Formula 1]

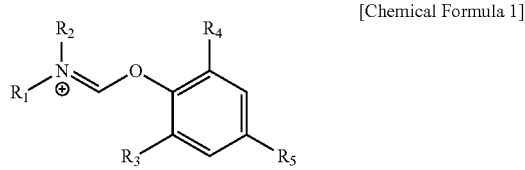

[Chemical Formula 4]

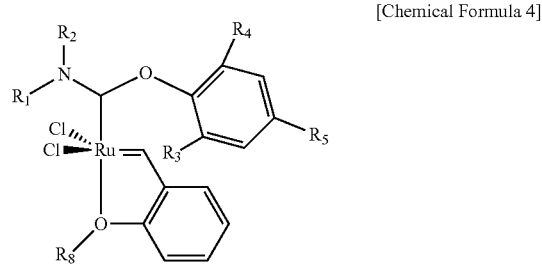

wherein, in the above Chemical Formulae,
$R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected,
$R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group,
$R_5$ is a hydrogen atom or $C_1$-$C_6$ alkyl group, and
$R_8$ is a substituted or unsubstituted $C_1$-$C_{10}$ alkyl group, $C_5$-$C_{10}$ carbocycle, or 5- to 10-membered heterocycle.

Specifically, the step of obtaining the ligand may be a step of obtaining an acyclic carbene ligand having a structure of Chemical Formula 2, and the step of forming the ruthenium complex catalyst may be a step of forming a ruthenium complex catalyst having a structure of Chemical Formula 5:

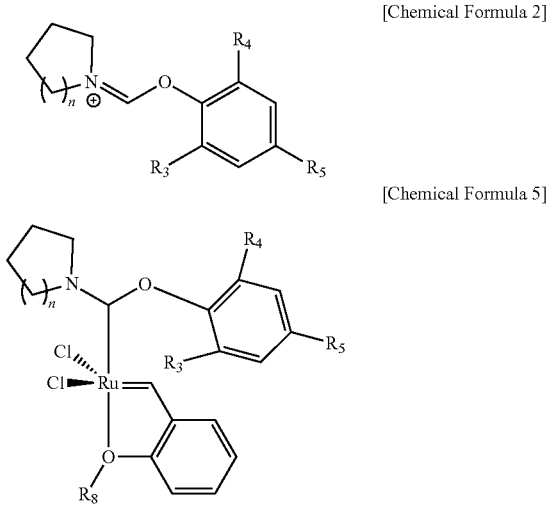

[Chemical Formula 2]

[Chemical Formula 5]

wherein, in the above Chemical Formulae, n is an integer of 0 to 4, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, and $R_8$ is a substituted or unsubstituted $C_1$-$C_{10}$ alkyl, $C_5$-$C_{10}$ carbocycle, or 5- to 10-membered heterocycle.

Specifically, the step of binding the ligand with ruthenium to form the ruthenium complex catalyst may be a step of preparing the ruthenium complex catalyst via a phosphine exchange reaction with a phosphine ruthenium catalyst, but is not limited thereto.

The acyclic carbene ligand and the ruthenium complex catalyst are the same as described above.

The intermediate produced by treating formamide with oxalyl chloride (($COCl)_2$) may be specifically chloromethyleneiminium, and more specifically, 1-(chloromethylene)pyrrolidin-1-rum.

To achieve the above object, still another aspect of the present invention provides a method of preparing linear alpha-olefins (linear α-olefins), the method including the step of reacting a linear or cyclic alkene compound in the presence of the ruthenium complex catalyst.

In this regard, the ruthenium, complex catalyst and the linear alpha-olefin are the same as described above.

The method of preparing linear alpha-olefins is characterized in that the linear or cyclic alkene compound as a reactant is reacted using the ruthenium complex catalyst, and thus linear alpha-olefins may be obtained in a high yield.

The reaction may be an ethylene-metathesis ethenolysis reaction, but is not limited thereto.

Hereinafter, the present invention will be described in more detail with reference to Examples. However, these Examples are for illustrative purposes only, and the scope of the present invention is not intended to be limited by these Examples.

Example 1: Preparation of Acyclic Carbene Ligand and Ruthenium Catalyst

Formamide was treated with oxalyl chloride, and then reacted with alkoxysilane to obtain an acyclic carbene ligand (L1-L12). The acyclic carbene ligand was subjected to a phosphine exchange reaction with a phosphine ruthenium catalyst to synthesize a novel ruthenium catalyst. Detailed procedures and reaction conditions for each step are described below.

Example 1-1: Preparation of Acyclic Carbene Ligand

Formamide (1 equiv.) was dissolved in dichloromethane (DCM), and then oxalyl chloride (($COCl)_2$, 1.5 equiv.) was added dropwise to the solution at −78° C., and this mixture was heated to room temperature and stirred for 1 hr. After removing the solvent, the product was dissolved again in DCM, and a DCM solution of alkoxysilane (ROTMS, 1 equiv.) was added dropwise at −78° C., and this mixture was heated to room temperature and stirred for 4 hr. Thereafter, the mixture was recrystallized from hexane to obtain each ligand compound of L1 to L12.

The obtained ligand compounds, L1 to L12, are as in Table 1 below.

TABLE 1

| Ligand compound | Structural formula |
|---|---|
| L1 | (structure with iPr, iPr, Cl⁻) |
| L2 | (structure with methyl groups, PF₆⁻) |
| L3 | (structure with Ph groups) |
| L4 | (structure with n-Pr, t-Bu, OTf⁻) |

TABLE 1-continued

| Ligand compound | Structural formula |
|---|---|
| L5 | (2,3-dihydroindol-1-ium methylene 2,6-diisopropylphenoxy, Cl⁻) |
| L6 | (2,6-dimethylpiperidin-1-ium methylene 2,6-diisopropylphenoxy, PF$_6^-$) |
| L7 | (piperidin-1-ium methylene 2,6-diisopropylphenoxy, Cl⁻) |
| L8 | (piperidin-1-ium methylene 2-n-propyl-6-tert-butylphenoxy, OTf⁻) |
| L9 | (N-isopropyl-N-(4-tert-butylphenyl)iminium methylene 2,6-diisopropylphenoxy, Cl⁻) |
| L10 | (N-isopropyl-N-(4-methoxyphenyl)iminium methylene 2,6-diisopropylphenoxy, Cl⁻) |
| L11 | (N-isopropyl-N-(4-fluorophenyl)iminium methylene 2,6-diisopropylphenoxy, Cl⁻) |
| L12 | (N-isopropyl-N-(4-trifluoromethylphenyl)iminium methylene 2,6-diisopropylphenoxy, Cl⁻) |

Example 1-2: Synthesis of Novel Ruthenium Catalyst

A novel ruthenium catalyst was synthesized using each of the ligand compounds. Each of the compounds L1 to L12 (2 equiv.) and a benzene solution of potassium bis(trimethylsilyl)amide (KHMDS, 2.2 eq.) were stirred at room temperature for 30 min. This solution was filtered and added to a benzene solution of a phosphine ruthenium catalyst. This mixture was filtered through a pad of Celite and extracted with benzene, and then the filtrate was concentrated. Thereafter, purification was performed by column chromatography, and each of the novel ruthenium catalyst compounds, Ru1 to Ru14, were obtained.

The compound names of the ruthenium catalyst compounds, Ru1 to Ru14, are shown in Tables 2 and 3.

TABLE 2

| Compound | Name of compound |
|---|---|
| Ru1 | Dichloro[(2,6-diisopropylphenoxy) (pyrrolidin-1-ium-1-ylidene)methanide] (2-isopropoxyphenylmethylene) ruthenium(II) |
| Ru2 | Dichloro[(2,6-dibenzhydryl-4-methylphenoxy) (pyrrolidin-1-ium-1-ylidene)methanide] (2-ispropoxyphenylmethylene) ruthenium(II) |
| Ru3 | Dichloro[(2-(tert-butyl)-6-propylphenoxy) (pyrrolidin-1-ium-1-ylidene)methanide] (2-isopropoxyphenylmethylene) ruthenium(II) |
| Ru6 | Dichloro[(2,6-diisopropylphenoxy) (piperidin-1-ium-1-ylidene)methanide] (2-isopropoxyphenylmethylene) ruthenium(II) |
| Ru8 | Dichloro[(2,6-diisopropylphenoxy) (pyrrolidin-1-ium-1-ylidene)methanide] (2-phenoxyphenylmethylene) ruthenium(II) |

TABLE 2-continued

| Compound | Name of compound |
|---|---|
| Ru9 | Dichloro[(Z)-(2,6-diisopropylphenoxy) ((2R,6S)-2,6-dimethylpiperidin-1-ium-1-ylidene)methanide] (2-phenoxyphenylmethylene) ruthenium(II) |
| Ru10 | Dichloro[(2,6-diisopropylphenoxy) (piperidin-1-ium-1-ylidene)methanide] (2-phenoxyphenylmethylene) ruthenium(II) |
| Ru11 | Dichloro[N-((2,6-diisopropylphenoxy) methaneidylene)-N-isopropylbenzenaminium] (2-phenoxyphenylmethylene) ruthenium(II) |
| Ru12 | Dichloro[4-(tert-butyl)-N-((2,6-diisopropylphenoxy) methaneidylene)-N-isopropylbenzenaminium] (2-phenoxyphenylmethylene) ruthenium(II) |
| Ru13 | Dichloro[N-((2,6-diisopropylphenox)methaneidylene)-4-fluoro-N-isopxopylbenzenaminium] (2-phenoxyphenylmethylene) ruthenium(II) |
| Ru14 | Dichloro[N-((2,6-diisopropylphenoxy)methaneidylene)-N-isopropyl-4-methoxybenzenaminium] (2-phenoxyphenylmethylene) ruthenium(II) |

TABLE 3

| Compound | Structural formula | NMR | Yield |
|---|---|---|---|
| Ru1 | | $^1$H NMR (400 MHz, CD$_2$Cl$_2$) δ 15.69 (s, 1H), 7.59-7.50 (m, 1H), 7.50-7.41 (m, 1H), 7.30 (dd, J = 7.7 Hz, 2.7 Hz, 2H), 6.92 (dq, J = 10.1 Hz, 8.0 Hz, 3H), 5.15 (dt, J = 9.7 Hz, 6.0 Hz, 1H), 4.81 (dd, J = 6.5 Hz, 4.5 Hz, 2H), 4.04 (t, J = 5.9 Hz, 2H), 3.18 (td, J = 11.0 Hz, 6.7 Hz, 2H), 2.20 (dt, J = 11.0 Hz, 5.5 Hz, 2H), 2.06 (dd, J = 12.5 Hz, 7.1 Hz, 2H), 1.72 (dd, J = 6.0 Hz, 2.8 Hz, 6H), 1.12 (dd, J = 6.8 Hz, 2.8 Hz, 6H), 0.92 (dd, J = 6.7 Hz, 2.7 Hz, 6H). | 51% |
| Ru2 | | $^1$H NMR (400 MHz, CD$_2$Cl$_2$) δ 16.33 (s, 1H), 7.67-7.59 (m, 1H), 7.16 (dd, J = 10.1 Hz, 4.6 Hz, 4H), 7.13-7.04 (m, 9H), 7.05-6.98 (m, 4H), 6.95 (t, J = 7.4 Hz, 1H), 6.86 (dd, J = 7.5 Hz, 1.6 Hz, 1H), 6.76 (dd, J = 6.6, 3.0 Hz, 4H), 6.58 (s, 2H), 5.90 (s, 2H), 4.64 (t, J = 6.8 Hz, 2H), 2.24 (s, 3H), 1.94 (p, J = 6.8 Hz, 2H), 1.80 (dd, J = 12.9 Hz, 6.8 Hz, 8H), 1.38 (p, J = 6.9 Hz, 2H). | 62% |
| Ru3 | | $^1$H NMR (400 MHz, CD$_2$Cl$_2$) δ 15.91 (s, 1H), 7.60-7.46 (m, 2H), 7.36 (t, J = 7.7 Hz, 1H), 7.11 (dd, J = 7.4 Hz, 1.5 Hz, 1H), 7.06-6.88 (m, 3H), 5.19 (dt, J = 12.3 Hz, 6.1 Hz, 1H), 4.89 (tdd, J = 17.0 Hz, 10.0 Hz, 6.9 Hz, 2H), 4.12-3.93 (m, 2H), 2.64 (ddd, J = 15.0 Hz, 8.6 Hz, 6.6 Hz, 1H), 2.38-2.26 (m, 1H), 2.21 (qd, J = 12.0 Hz, 6.2 Hz, 2H), 2.11-2.00 (m, 2H), 1.76 (dd, J = 6.1 Hz, 1.7 Hz, 6H), 1.52-1.41 (m, 2H), 1.34 (s, 9H), 0.92-0.76 (m, 3H). | 37% |

TABLE 3-continued

| Compound | Structural formula | NMR | Yield |
|---|---|---|---|
| Ru6 | | ¹H NMR (400 MHz, CD₂Cl₂) δ 15.64 (d, J = 16.0 Hz, 1H), 7.58-7.50 (m, 1H), 7.49-7.42 (m, 1H), 7.29 (d, J = 7.7 Hz, 2H), 6.97-6.85 (m, 3H), 5.11 (dq, J = 12.2 Hz, 6.1 Hz, 1H), 4.57-4.45 (m, 2H), 4.07-3.96 (m, 2H), 3.18 (hept, J = 6.9 Hz, 2H), 2.15-2.03 (m, 2H), 1.85 (dt, J = 11.8 Hz, 5.7 Hz, 2H), 1.76-1.62 (m, 8H), 1.10 (d, J = 6.9 Hz, 6H), 0.94 (d, J = 6.8 Hz, 6H). | 33% |
| Ru8 | | ¹H NMR (400 MHz, CD₂Cl₂) δ 15.76 (d, J = 11.4 Hz, 1H), 7.54-7.39 (m, 6H), 7.39-7.31 (m, 3H), 7.02-6.95 (m, 2H), 6.63 (d, J = 8.3 Hz, 1H), 4.54 (t, J = 6.6 Hz, 2H), 4.02 (t, J = 7.1 Hz, 2H), 3.19 (dt, J = 13.7 Hz, 6.8 Hz, 2H), 2.14-1.93 (m, 4H), 1.14 (d, J = 6.9 Hz, 6H), 0.96 (d, J = 6.8 Hz, 6H). | 18% |
| Ru9 | | ¹H NMR (400 MHz, CD₂Cl₂) δ 15.79 (d, J = 0.9 Hz, 1H), 7.53-7.38 (m, 6H), 7.39-7.29 (m, 3H), 7.01-6.93 (m, 2H), 6.59 (d, J = 8.3 Hz, 1H), 5.10 (dd, J = 14.9 Hz, 10.7 Hz, 1H), 5.01-4.88 (m, 1H), 3.24 (dt, J = 13.6 Hz, 6.8 Hz, 1H), 3.12 (dt, J = 13.6 Hz, 6.8 Hz, 1H), 2.30 (td, J = 12.8 Hz, 6.6 Hz, 1H), 2.01 (dt, J = 12.0 Hz, 7.2 Hz, 1H), 1.90-1.77 (m, 1H), 1.75-1.56 (m, 6H), 1.41 (d, J = 7.2 Hz, 3H), 1.12 (dd, J = 6.9 Hz, 2.6 Hz, 6H), 0.98 (dd, J = 6.8 Hz, 3.3 Hz, 6H). | 28% |
| Ru10 | | ¹H NMR (400 MHz, CD₂Cl₂) δ 15.72 (d, J = 13.8 Hz, 1H), 7.51-7.40 (m, 6H), 7.37-7.31 (m, 3H), 6.98 (d, J = 4.3 Hz, 2H), 6.60 (d, J = 8.3 Hz, 1H), 4.30-4.14 (m, 2H), 4.05-3.93 (m, 2H), 3.19 (dt, J = 13.7 Hz, 6.8 Hz, 2H), 2.00-1.87 (m, 2H), 1.84-1.73 (m, 2H), 1.73-1.61 (m, 2H), 1.12 (d, J = 6.9 Hz, 6H), 0.98 (d, J = 6.8 Hz, 6H). | 28% |

TABLE 3-continued

| Compound | Structural formula | NMR | Yield |
|---|---|---|---|
| Ru11 | | ¹H NMR (400 MHz, CD₂Cl₂) δ 15.70 (s, 1H), 7.57-7.31 (m, 9H), 7.29-7.16 (m, 4H), 7.05-6.91 (m, 2H), 6.63 (d, J = 8.3 Hz, 1H), 5.14 (dt, J = 12.4 Hz, 6.2 Hz, 1H), 3.19 (dt, J = 13.6 Hz, 6.8 Hz, 2H), 1.45 (d, J = 6.3 Hz, 6H), 0.93 (dd, J = 40.0 Hz, 6.8 Hz, 12H). | 53% |
| Ru12 | | ¹H NMR (400 MHz, CD₂Cl₂) δ 15.75 (d, J = 0.7 Hz, 1H), 7.59-7.33 (m, 7H), 7.28 (t, J = 13.8 Hz, 2H), 7.14 (t, J = 14.2 Hz, 2H), 7.05-6.91 (m, 2H), 6.63 (d, J = 8.3 Hz, 1H), 5.20-4.98 (m, 1H), 3.19 (dt, J = 13.4 Hz, 6.7 Hz, 2H), 1.44 (d, J = 6.2 Hz, 6H), 1.06-0.77 (m, 12H). | 43% |
| Ru13 | | ¹H NMR (400 MHz, CD₂Cl₂) δ 5.66 (d, J = 0.7 Hz, 1H), 7.70-7.34 (m, 7H), 7.34-7.06 (m, 6H), 7.06-6.93 (m, 2H), 6.66 (dd, J = 20.5 Hz, 8.5 Hz, 1H), 5.12 (dt, J = 12.5 Hz, 6.2 Hz, 1H), 3.16 (dt, J = 13.6 Hz, 6.8 Hz, 2H), 1.46 (t, J = 13.2 Hz, 6H), 1.14-0.79 (m, 12H). | 35% |

TABLE 3-continued

| Compound | Structural formula | NMR | Yield |
|---|---|---|---|
| Ru14 | (structure shown) | $^1$H NMR (400 MHz, CD$_2$Cl$_2$) δ 15.72 (d, J = 0.5 Hz, 1H), 7.58-7.29 (m, 9H), 7.26 (t, J = 6.6 Hz, 2H), 7.20-7.07 (m, 3H), 7.03-6.87 (m, 5H), 6.75-6.58 (m, 2H), 5.09 (dt, J = 12.4 Hz, 6.2 Hz, 1H), 3.77 (s, 3H), 3.18 (dt, J = 13.6 Hz, 6.8 Hz, 2H), 1.41 (t, J = 11.7 Hz, 6H), 1.01-0.76 (m, 12H). | 43% |

Example 2. Measurement of Selectivity and Turnover Number of Ruthenium Catalyst Compound for Ethenolysis The selectivity and the turnover number of each of the ruthenium catalyst compounds Ru1 to Ru14 prepared in Example 1 for an ethenolysis reaction were measured by the following methods.

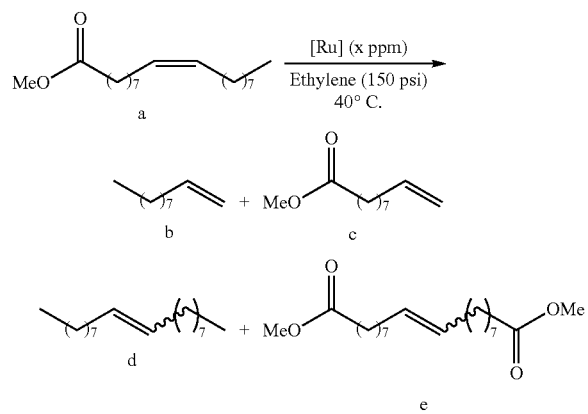

In this regard,

Conversion was calculated as Conversion (%)=[1−(final number of moles of compound $a$)/(initial number of moles of compound $a$)]×100, Selectivity was calculated as Selectivity (%)=(Total number of moles of compounds $b$ and $c$)/[(Total number of moles of compounds $b$ and $c$)+(Total number of moles of compounds $d$ and $e$)×2], Yield was calculated as Yield (%)=Conversion×Selectivity/100, and Turnover number was calculated as Turnover number=Yield×(initial number of moles of $a$/number of moles of catalyst)/100.

The results are shown in Table 4 below.

TABLE 4

| Ruthenium catalyst compound | Loading (ppm) | Conversion (%) | Selectivity (%) | Yield (%) | Turnover number |
|---|---|---|---|---|---|
| Ru1 | 50 | 80 | 90 | 72 | 14,000 |
|  | 10 | 37 | 91 | 33 | 33,000 |
| Ru2 | 50 | 51 | 89 | 45 | 9000 |
|  | 10 | 19 | 86 | 17 | 17,000 |
| Ru3 | 50 | 86 | 91 | 73 | 16,000 |
|  | 10 | 70 | 95 | 67 | 67,000 |
|  | 5 | 52 | 97 | 50 | 100,0 |
| Ru4 | 10 | 16 | 90 | 14 | 14,000 |
| Ru5 | 50 | 4 | 93 | 4 | 800 |
| Ru6 | 50 | 82 | 89 | 73 | 14,500 |
|  | 10 | 5 | 88 | 4 | 4,000 |
| Ru8 | 50 | 23 | 52 | 12 | 12,000 |
| Ru9 | 50 | 45 | 84 | 37 | 7,500 |
| Ru10 | 50 | 52 | 86 | 45 | 9,001 |
| Ru11 | 50 | 55 | 84 | 46 | 9,200 |
| Ru12 | 50 | 49 | 85 | 41 | 8,300 |
| Ru13 | 50 | 48 | 87 | 42 | 8,400 |
| Ru14 | 50 | 57 | 85 | 48 | 9,700 |

It was confirmed than the selectivity and turnover number of the prepared ruthenium catalyst compounds for the ethenolysis reaction were increased, and thus the yield of linear alpha-olefins was increased. In particular, it was confirmed that as the ring structure including the nitrogen atom of carbene was formed, the selectivity and turnover number were increased.

Comparative Example: Preparation of Acyclic Carbene Ligand and Ruthenium Catalyst For comparison with the acyclic aminooxycarbene compounds, ruthenium catalyst compounds Ru15 and Ru16 were prepared by the method of Example 1-2, and the selectivity and turnover number of each compound for the ethenolysis reaction were measured.

The structure of each compound is shown in Table 5 below, and the selectivity and turnover number thereof are shown in Table 6.

TABLE 5

| Compound | Structural formula | NMR | Yield |
|---|---|---|---|
| Ru15 | (structure with i-Pr, N, O, Cl, Ru groups) | $^1$H NMR (400 MHz, CD$_2$Cl$_2$) δ 15.64 (d, J = 0.8 Hz, 1H), 7.58-7.51 (m, 1H), 7.51-7.44 (m, 1H), 7.36-7.30 (m, 2H), 6.93 (t, J = 6.7 Hz, 1H), 6.90-6.86 (m, 2H), 5.25 (dt, J = 12.4 Hz, 6.2 Hz, 1H), 5.17-5.00 (m, 1H), 3.74 (hept, J = 6.8 Hz, 1H), 3.13 (hept, J = 7.0 Hz, 2H), 1.67 (dd, J = 6.2 Hz, 1.1 Hz, 12H), 1.54 (d, J = 6.9 Hz, 6H), 1.11 (d, J = 6.9 Hz, 6H), 0.86 (d, J = 6.7 Hz, 6H). | 70% |
| Ru16 | (structure with phenyl, i-Pr, N, O, Cl, Ru groups) | $^1$H NMR (400 MHz, CD$_2$Cl$_2$) δ 15.58 (d, J = 0.6 Hz, 1H), 7.62-7.53 (m, 1H), 7.47-7.33 (m, 4H), 7.29-7.17 (m, 4H), 6.99 (d, J = 8.4 Hz, 1H), 6.95-6.85 (m, 2H), 5.60-5.45 (m, 1H), 5.18 (dq, J = 12.3 Hz, 6.1 Hz, 1H), 3.18 (hept, J = 6.9 Hz, 2H), 1.74 (d, J = 6.1 Hz, 6H), 1.58 (d, J = 6.3 Hz, 6H), 0.89 (dd, J = 35.9 Hz, 6.8 Hz, 12H). | 65% |

TABLE 6

| Ruthenium catalyst compound | Loading (ppm) | Conversion (%) | Selectivity (%) | Yield (%) | Turnover number |
|---|---|---|---|---|---|
| Ru15 | 50 | 1 | 92 | 1 | 230 |
| Ru16 | 10 | 0.9 | N.D. | 0.9 | 900 |

As described above, it was confirmed that the catalyst compounds of the present invention showed remarkable selectivity and turnover number for the ethenolysis reaction, as compared with the ruthenium catalyst compound of Ru15 or Ru16.

Experimental Example: X-Ray Crystal Analysis

Figure 2A:
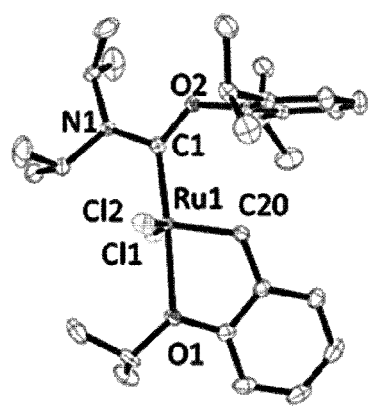
FIG. 2A shows the result of X-ray crystal analysis of a ruthenium complex catalyst.

In order to investigate the solid-phase structure of the ruthenium catalyst single crystal by X-ray analysis, the structures of the ruthenium catalyst compounds Ru15 and Ru3 prepared in Example 2 and the Comparative Example were analyzed by X-ray crystallization. The results are shown in FIGS. 2A and 2B.

Figure 2B:
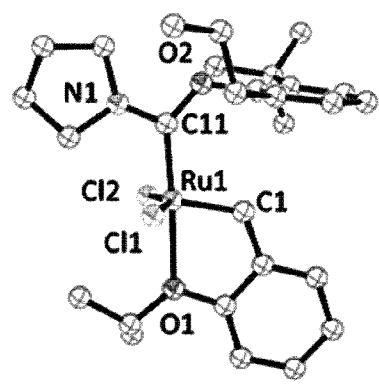
FIG. 2B shows the result of X-ray crystal analysis of a ruthenium complex catalyst.

As a result, the selected bond length (Å) and bond angle (°) are as follows:

it was confirmed that the bond lengths and the bond angles of the ruthenium catalyst compound Ru15 were Ru—C1=1.956(2) Å, Ru=C20=1.835(2) Å, Ru–O1=2.232(1) Å, ∠N1-C1-O2=109.5(1)°, ∠N1-C1-Ru=117.0(1)°, and ∠Cl—Ru—Cl=157.09(3)° (FIG. 2A), and the bond lengths and the bond angles of the ruthenium catalyst compound Ru3 were Ru—C11=1.959(2) Å, Ru=C1=1.827(3) Å, Ru–O1=2.264(2) Å, ∠N1-C11-O2=108.0(2)°, ∠N1-C11-Ru=117.0(2)°, and ∠Cl—Ru—Cl=152.61(3)° (FIG. 2B).

As a result, the ruthenium catalyst compounds Ru15 and Ru3 showed a distorted square-pyramidal structure, and had a structure in which the Iv-aryl group is located, above O-benzylidene. In particular, it was confirmed that the angle of N—C—O was greater than that of the existing cyclic carbene N—C—N (103-104°). Due to the increased angle, the acyclic carbene ligand of the present invention has excellent, electron-donating ability, and may help to improve selectivity due to the three-dimensional effect.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

Effect of the Invention

An acyclic carbene ligand of the present invention and a ruthenium complex catalyst using the same have high selectivity and turnover number for terminal olefin formation in an ethylene-metathesis ethenolysis reaction, and thus linear α-olefins may be prepared with a high yield.

What is claimed is:

1. An acyclic carbene ligand for the formation of a ruthenium complex, the acyclic carbene ligand having a structure of Chemical Formula 2:

[Chemical Formula 2]

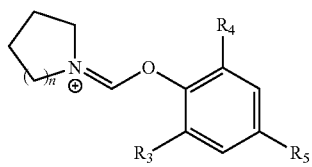

wherein, in Chemical Formula 2, n is an integer of 0 to 4, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, and $R_5$ is a hydrogen atom or $C_1$-$C_6$ alkyl group.

2. The acyclic carbene ligand of claim 1, wherein n is an integer of 1 or 2, and $R_3$ and $R_4$ are each independently propyl, butyl, or diphenylmethyl.

3. A ruthenium complex catalyst having a structure of Chemical Formula 3:

[Chemical Formula 3]

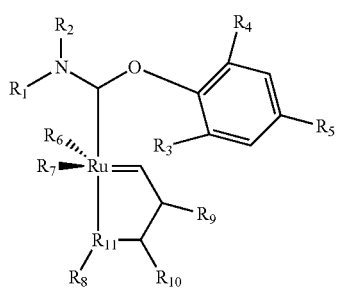

wherein, in Chemical Formula 3, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, $R_6$ and $R_7$ are each independently a halogen, $R_8$ is a substituted or unsubstituted $C_1$-$C_{10}$ alkyl group, $C_5$-$C_{10}$ carbocycle, or 5- to 10-membered heterocycle, $R_9$ and $R_{10}$ are each independently a $C_1$-$C_{10}$ alkyl group, or are connected to each other to form a $C_5$-$C_{10}$ carbocycle or a 5- to 10-membered heterocycle, and $R_{11}$ is N or O.

4. The ruthenium complex catalyst of claim 3, wherein the ruthenium complex catalyst has a structure of the following Chemical Formula 4:

[Chemical Formula 4]

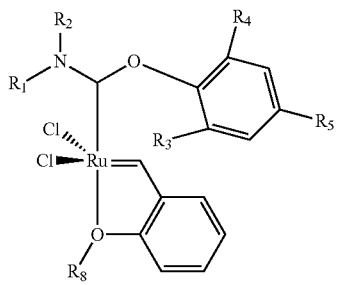

wherein, in Chemical Formula 4, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, and $R_8$ is a substituted or unsubstituted $C_1$-$C_{10}$ alkyl group, $C_5$-$C_{10}$ carbocycle, or 5- to 10-membered heterocycle.

5. The ruthenium complex catalyst of claim 4, wherein the ruthenium complex catalyst has a structure of Chemical Formula 5:

[Chemical Formula 5]

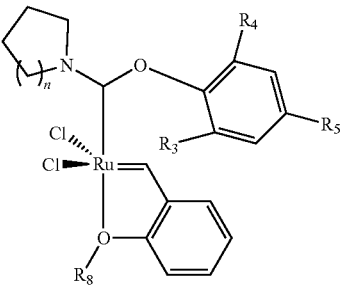

wherein, in Chemical Formula 5, n is an integer of 0 to 4, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, and $R_8$ is a substituted or unsubstituted $C_1$-$C_{10}$ alkyl group, $C_5$-$C_{10}$ carbocycle, or 5- to 10-membered heterocycle.

6. The ruthenium complex catalyst of claim 5, wherein n is an integer of 1 or 2, and $R_3$ and $R_4$ are each independently propyl, butyl, or diphenylmethyl.

7. A method of using the ruthenium complex of claim 3 as a catalyst in an ethylene-metathesis ethenolysis reaction of a linear or cyclic alkene compound.

8. A method of preparing a ruthenium complex catalyst, the method comprising the steps of:

treating formamide with oxalyl chloride to obtain an intermediate;

reacting the intermediate with alkoxysilane to obtain an acyclic carbene ligand having a structure of Chemical Formula 1; and binding the ligand with ruthenium to form a ruthenium complex catalyst having a structure of Chemical Formula 4:

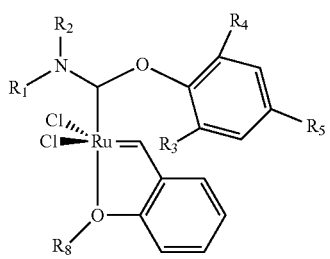

[Chemical Formula 1]

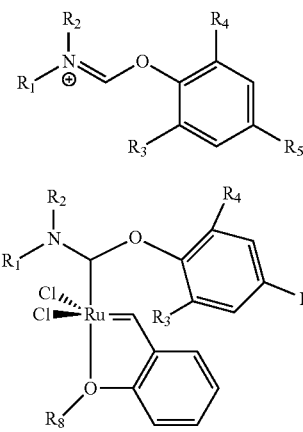

[Chemical Formula 4]

wherein, in the above Chemical Formulae, $R_1$ and $R_2$ are each independently a hydrogen atom, a substituted or unsubstituted $C_1$-$C_6$ alkyl group, $C_3$-$C_8$ cycloalkyl group, or $C_6$-$C_{10}$ aryl group; or $R_1$ and $R_2$ are connected to each other to form an unsubstituted or substituted 4- to 8-membered heterocycle with a nitrogen atom to which they are connected, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, and $R_8$ is a substituted or unsubstituted $C_1$-$C_{10}$ alkyl group, $C_5$-$C_{10}$ carbocycle, or 5- to 10-membered heterocycle.

9. The method of claim 8, wherein the step of obtaining the ligand is a step of obtaining an acyclic carbene ligand having a structure of Chemical Formula 2, and the step of forming the ruthenium complex catalyst is a step of forming a ruthenium complex catalyst having a structure of Chemical Formula 5:

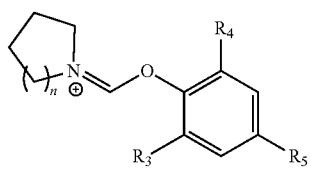

[Chemical Formula 2]

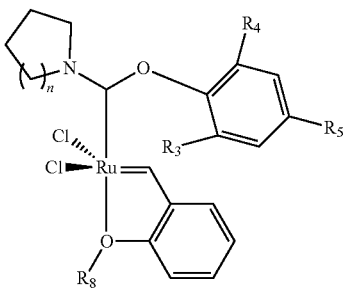

[Chemical Formula 5]

wherein, in the above Chemical Formulae, n is an integer of 0 to 4, $R_3$ and $R_4$ are each independently a hydrogen atom, a substituted or unsubstituted $C_1$-$C_6$ alkyl group, $C_1$-$C_6$ alkenyl group, $C_1$-$C_6$ alkynyl group, $C_3$-$C_8$ cycloalkyl group, or $C_6$-$C_{10}$ aryl group, $R_5$ is a hydrogen atom or $C_1$-$C_6$ alkyl group, and $R_8$ is a substituted or unsubstituted $C_1$-$C_{10}$ alkyl, $C_5$-$C_{10}$ carbocycle, or 5- to 10-membered heterocycle.

10. The method of claim 8, wherein the step of binding the ligand with ruthenium to form a ruthenium complex catalyst is a step of forming a ruthenium complex catalyst via a phosphine exchange reaction with a phosphine ruthenium catalyst.

11. A method of preparing linear alpha-olefins, the method comprising the step of reacting a linear or cyclic alkene compound in the presence of the ruthenium complex catalyst of claim 3.

* * * * *